United States Patent
Ueno et al.

(10) Patent No.: US 8,609,729 B2
(45) Date of Patent: Dec. 17, 2013

(54) METHOD FOR TREATING MACULAR DEGENERATION

(75) Inventors: Ryuji Ueno, Potomac, MD (US); John Cuppoletti, Cincinnati, OH (US)

(73) Assignee: Sucampo AG, Zug (CH)

( * ) Notice: Subject to any disclaimer, the term of this patent is extended or adjusted under 35 U.S.C. 154(b) by 351 days.

(21) Appl. No.: 12/758,550

(22) Filed: Apr. 12, 2010

(65) Prior Publication Data

US 2010/0267832 A1   Oct. 21, 2010

Related U.S. Application Data

(60) Provisional application No. 61/169,512, filed on Apr. 15, 2009.

(51) Int. Cl.
| | |
|---|---|
| A01N 37/08 | (2006.01) |
| A01N 53/00 | (2006.01) |
| A01N 35/00 | (2006.01) |
| A01N 27/00 | (2006.01) |
| A61K 31/19 | (2006.01) |
| A61K 31/557 | (2006.01) |
| A61K 31/12 | (2006.01) |
| A61K 31/015 | (2006.01) |

(52) U.S. Cl.
USPC .......................... 514/573; 514/690; 514/763

(58) Field of Classification Search
None
See application file for complete search history.

(56) References Cited

U.S. PATENT DOCUMENTS

| | | | |
|---|---|---|---|
| 5,001,153 A * | 3/1991 | Ueno et al. | 514/530 |
| 5,151,444 A | 9/1992 | Ueno et al. | |
| 5,252,605 A | 10/1993 | Ueno | |
| 5,905,091 A | 5/1999 | Fuller | |
| 6,225,348 B1 * | 5/2001 | Paulsen | 514/530 |
| 2004/0254230 A1 * | 12/2004 | Ogidigben et al. | 514/381 |

FOREIGN PATENT DOCUMENTS

EP      0 453 127 A2     10/1991

OTHER PUBLICATIONS

Chemical Abstracts Services Registry No. 120373-24-2. Retrieved Dec. 30, 2011.*
Kashiwagi et al. "Effects of Isopropyl Unoprostone and Latanoprost on Melanogenesis in Mouse Epidermal Melanocytes", J.Glaucoma, 2002, vol. 11, pp. 57-64.*
New Zealand Examination Report dated Aug. 22, 2012, for corresponding Application No. 596035.
International Search Report with Written Opinion for Application No. PCT/JP2010/057108 dated Oct. 6, 2010.
Telander D G et al: Prostaglandins and Prostamides' Role in Melanin Synthesis in the Retinal Pigment Epithelium; ARVO Annual Meeting Abstract Search and Program Planner, vol. 2002, 2002.
Ladewig M S et al: Prostaglandin E1 infusion therapy in dry age-related macular degeneration; Prostaglandins, Leukotrienes and Essential Fatty Acids, Churchill Livingstone, Edinburgh LNKD-DOI: 10.1016/J.PLEFA.2004.11.006, vol. 72, No. 4, Apr. 1, 2005, pp. 251-256.

* cited by examiner

*Primary Examiner* — James D Anderson
*Assistant Examiner* — Stephanie Springer
(74) *Attorney, Agent, or Firm* — Sughrue Mion, PLLC

(57) ABSTRACT

Disclosed is a method for treating macular degeneration in a mammalian subject, which comprises administering to the subject in need thereof an effective amount of a 15-keto-prostaglandin compound such as 13,14-dihydro-15-keto-20-ethyl-prostaglandin $F_{2\alpha}$ isopropyl ester.

8 Claims, 2 Drawing Sheets

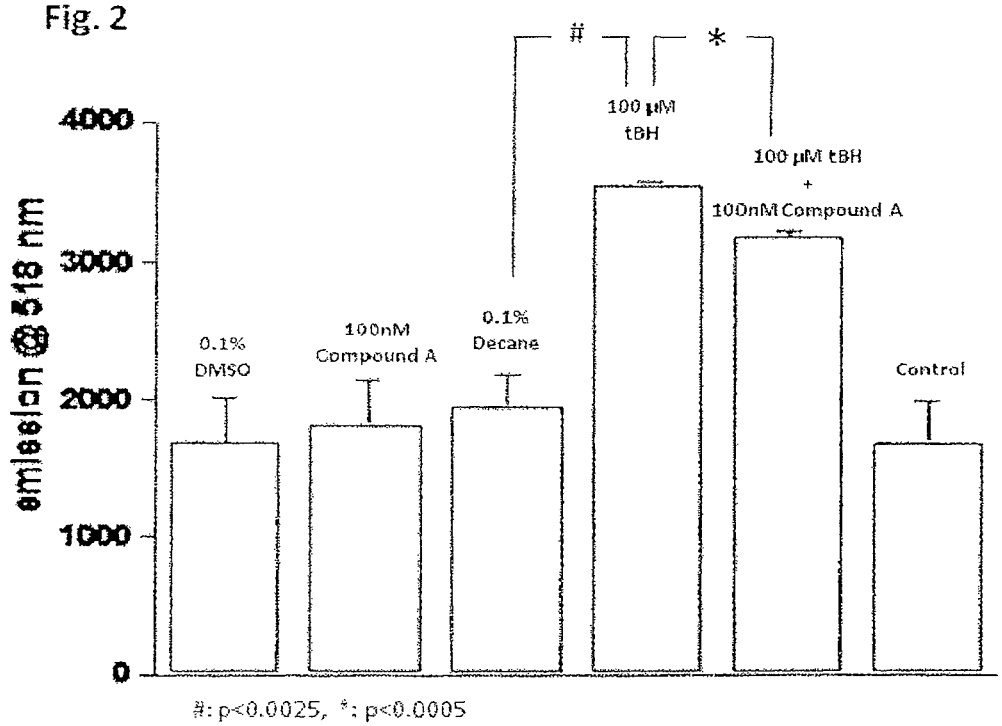

METHOD FOR TREATING MACULAR DEGENERATION

CROSS REFERENCE TO RELATED APPLICATION

This application claims the benefit of U.S. Provisional Application No. 61/169,512 filed Apr. 15, 2009. The whole contents of the provisional application is herein incorporated by reference.

TECHNICAL FIELD

The present invention relates to a method and composition for treating macular degeneration, especially age related macular degeneration, more especially dry age related macular degeneration.

BACKGROUND ART

Macular degeneration is caused by the deterioration of the central portion of the retina, the inside back layer of the eye that records the images we see and sends them via the optic nerve from the eye to the brain. The retina's central portion, known as the macula, is responsible for focusing central vision in the eye which controls our ability to read, drive a car, recognize faces or colors, and see objects in fine detail.

Age related macular degeneration (AMD) is the leading cause of legal blindness among people over 65. Persons suffering from AMD lose the ability to see fine details. The patient is able to see the edges of an image but the middle of the image is blank or appears as a dark spot called a scotoma. This condition can occur in one or both eyes.

There are two basic forms of AMD, known as "wet AMD" and "dry AMD". Dry AMD is also referred to as non-neovascular or non-exudative AMD. Approximately 85% to 90% of patients with AMD have the dry (atrophic) type AMD. Patients with this form AMD may have good central vision (20/40 or better) but substantial functional limitations. In dry AMD, the deterioration of the retina is associated with the formation of drusen under the macula. Drusen are accumulations of acellular (small yellow deposits), amorphous debris subjacent to the basement membrane of the retinal pigment epithelium. This phenomena leads to a thinning and drying out of the macula, causing the macula to lose its function. Currently, there is no known cure for Dry AMD and no approved pharmacological treatment for the condition. A strong need therefore exists for a treatment that reduces or limits macular degeneration.

Prostaglandins (hereinafter, referred to as PG(s)) are members of class of organic carboxylic acids, which are contained in tissues or organs of human or other mammals, and exhibit a wide range of physiological activities. PGs found in nature (primary PGs) have, as a general structural property thereof, a prostanoic acid skeleton as shown in the formula (A):

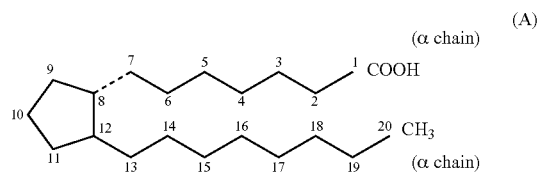

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

In addition, some 15-keto PGs (i.e. those having an oxo group at position 15 in place of the hydroxy group) and 13,14-dihydro (i.e. those having a single bond between positions 13 and 14) -15-keto-PGs are known as substances naturally produced by enzymatic actions during in vivo metabolism of primary PGs and have some therapeutic effect. For example, 15-keto-prostaglandin compounds have been known to be useful for the treatment of ocular hypertension and glaucoma (U.S. Pat. Nos. 5,001,153 and 5,151,444, These publications are incorporated herein by reference).

However it is not known how the 15-keto-prostaglandin compound acts on macular degeneration, especially AMD, more especially dry AMD.

DISCLOSURE OF THE INVENTION

An object of the present invention to provide a method and composition for treating macular degeneration, especially age related macular degeneration and more especially, dry age related macular degeneration in a mammalian subject including human.

The present invention relates to a method for treating macular degeneration in a mammalian subject, which comprises administering to the subject in need thereof an effective amount of a 15-keto-prostaglandin compound.

Especially the present invention relates to a method for treating age related macular degeneration in a mammalian subject, which comprises administering to the subject in need thereof an effective amount of a 15-keto-prostaglandin compound.

More especially the present invention relates to a method for treating dry age related macular degeneration in a mammalian subject, which comprises administering to the subject in need thereof an effective amount of a 15-keto-prostaglandin compound.

Further more, the present invention relates to a pharmaceutical composition for treating macular degeneration, especially age related macular degeneration and more especially, dry age related macular degeneration in a mammalian subject which comprises an effective amount of a 15-keto-prostaglandin compound.

The present invention also relates to use of a 15-keto prostaglandin compound for the manufacture of a pharmaceutical composition for treating macular degeneration, especially age related macular degeneration and more especially, dry age related macular degeneration in a mammalian subject.

BRIEF EXPLANATION OF DRAWINGS

FIG. 2 depicts a graph representing the effect of isopropyl unoprostone on the degeneration of the human retinal pigment epithelium cells caused by tert-butyl hydropoeroxide (tBH).

DETAILED DESCRIPTION OF THE INVENTION

Figure 1:
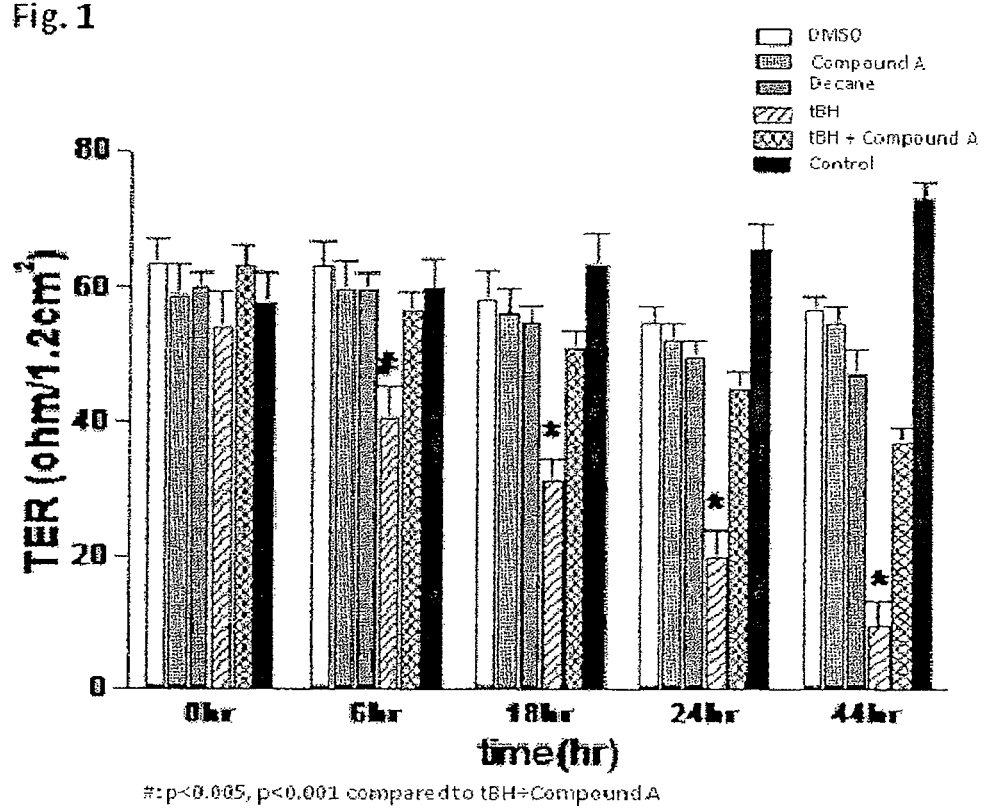
FIG. 1 depicts a graph representing the effect of isopropyl unoprostone on the loss of trans-epitherial resistance (TER) of the human retinal pigment epithelium cells caused by tert-butyl hydropoeroxide (tBH).

In the present invention, the "15-keto-prostaglandin compound" (hereinafter, referred to as "15-keto-PG compound") may include any of derivatives or analogs (including substituted derivatives) of a compound having an oxo group at 15-position of the prostanoic acid skeleton instead of the hydroxy group, irrespective of the configuration of the five-membered ring, the number of double bonds, presence or absence of a substituent, or any other modification in the α or ω chain.

The nomenclature of the 15-keto-PG compounds used herein is based on the numbering system of the prostanoic acid represented in the above formula (A).

The formula (A) shows a basic skeleton of the C-20 carbon atoms, but the 15-keto-PG compounds in the present invention are not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-deoxy-PG compound.

As stated above, the nomenclature of the 15-keto-prostaglandin compounds is based on the prostanoic acid skeleton. However, in case the compound has a similar partial construction as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-15-keto-PG compound. Similarly, a PG compound having 11 carbon atoms in the α-chain is named as 2-decarboxy-2-(4-carboxybutyl)-15-keto-PGF compound. Further, a PG compound of which ω-chain is extended by two carbon atoms, that is, having 10 carbon atoms in the ω-chain is named as 15-keto-20-ethyl-PG compound. These compounds, however, may also be named according to the IUPAC nomenclatures.

The 15-keto-PGs used in the present invention may include any PG derivatives or analogs insofar as having an oxo group at position 15 in place of the hydroxy group. Accordingly, for example, a 15-keto-PG type 1 compound having a double bond at 13-14 position, a 15-keto-PG type 2 compound having two double bond at 13-14 and 5-6 position, a 15-keto-PG type 3 compound having three double bond at 5-6, 13-14 and 17-18 position, 13,14-dihydro-15-keto-PG compound wherein the double bond at 13-14 position is single bond.

Typical examples of the compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives or analogs thereof.

Examples of the analogs (including substituted derivatives) or derivatives include a 15-keto-PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy(lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 and 11 may be α, β or a mixture thereof.

Further, the above analogs may be compounds having an alkoxy, cycloalkyl, cycloalkyloxy, phenoxy or phenyl group at the end of the ω-chain where the chain is shorter than the primary PGs.

Especially preferred compounds include a 13,14-dihydro-15-keto-PG compound which has a single bond at position 13-14; a compound of which ω-chain is extended.

A preferred compounds used in the present invention is represented by the formula (I):

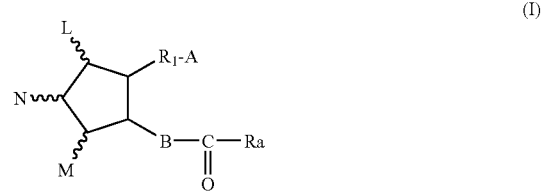

(I)

wherein L, M and N are hydrogen, hydroxy, halogen, lower alkyl, hydroxy(lower)alkyl, or oxo, and the five-membered ring may have at least one double bond;

A is —CH$_3$, —CH$_2$OH, —COCH$_2$OH, —COOH or a functional derivative thereof;

B is —CH$_2$—CH$_2$-, —CH=CH— or

R$_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon group, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy, lower aklanoyloxy, cyclo(lower)alkyl; cyclo(lower) alkyloxy; aryl; aryloxy; heterocyclic group; heterocyclic-oxy group.

A group of particularly preferable compounds among the above described compounds is represented by the formula (II):

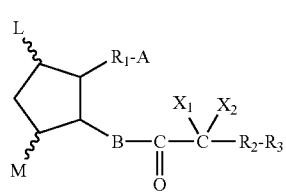

wherein L and M are hydrogen, hydroxy, halogen, lower alkyl, hydroxy(lower)alkyl lower alkanoyloxy or oxo, and the five-membered ring may have at least one double bond;

A is —$CH_3$, —$CH_2OH$, —$COCH_2OH$, —COOH or a functional derivative thereof;

B is —$CH_2$—$CH_2$—, —CH=CH—, —C≡C—;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

$R_2$ is a single bond or lower alkylene; and $R_3$ is lower alkyl, lower alkoxy, lower alkanoyloxy, cyclo (lower)alkyl, cyclo(lower)alkyloxy, aryl, aryloxy, heterocyclic group or heterocyclic-oxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M are a combination wherein both of them are hydroxy which has a 5-membered ring structure of, so called, PGF type; a combination wherein L is hydroxy and M is oxo which has a 5-membered ring structure of, so called, PGE type, and a combination wherein L is oxo and M is hydrogen which has a 5-membered ring structure of, so called, 11-deoxy-PG type.

Preferred example A is —COOH, its pharmaceutically acceptable salt, ester or amide thereof.

Preferred example B is —CH$_2$—CH$_2$—, which provides the structure of so-called, 13,14-dihydro type.

Preferred example of X$_1$ and X$_7$ are hydrogen or halogen, preferably at least one of them is halogen, more preferably, both of them are halogen, especially, fluorine that provides a structure of, so called 16,16-difluoro type.

Preferred R$_1$ is a hydrocarbon containing 1-10 carbon atoms, preferably, 6-10 carbon atoms. Further, at least one carbon atom in the aliphatic hydrocarbon is optionally substituted by oxygen, nitrogen or sulfur.

Examples of R$_1$ include, for example, the following groups:
—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—O—CH$_2$—,
—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—CH$_2$—,
—CH$_2$—CH$_2$—CH$_2$—CH$_2$—CH$_2$—CH$_2$—CH=CH—,
—CH$_2$—C≡C—CH$_2$—CH$_2$—CH$_2$—CH$_2$—CH$_2$—, and
—CH$_2$—CH$_2$—CH$_2$—CH$_2$—CH$_2$—CH$_2$—CH(CH$_3$)—CH$_2$—.

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

The Examples of the typical compound in the invention is 13,14-dihydro-15-keto-20-ethyl PGF compound, and the derivatives or analogs thereof. The example of most preferable compound in the invention is 13,14-dihydro-15-keto-20-ethyl F$_{2\alpha}$ isopropyl ester (hereinafter, it is also referred to as "isopropyl unoprostone").

In the present invention, the PG compound which is dihydro between 13 and 14, and keto(=O) at 15 position may be in the keto-hemiacetal equilibrium by formation of a hemiacetal between hydroxy at position 11 and keto at position 15.

For example, it has been revealed that when both of X$_1$ and X$_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

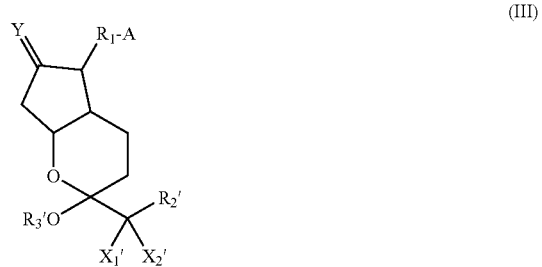

wherein, A is —CH$_3$, or —CH$_2$OH, —COCH$_2$OH, —COOH or a functional derivative thereof;
X$_1$' and X$_2$' are hydrogen, lower alkyl, or halogen;
Y is

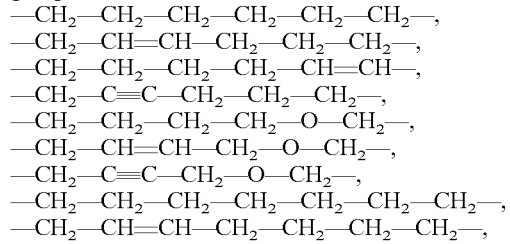

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

According to the present invention, a mammalian subject may be treated by the instant invention by administering the compound used in the present invention. The subject may be any mammalian subject including a human. The compound can be applied systemically or topically. Usually, the compound may be administered by oral administration, intravenous injection (including infusion), ocular topical administration (e.g. periocular (e.g., subTenon's), subconjunctival, intraocular, intravitreal, intracameral, subretinal, suprachoroidal, and retrobulbar administrations) and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.00001-500 mg/kg per day, more preferably 0.0001-100 mg/kg per day.

The compound may preferably be formulated in a pharmaceutical composition suitable for administration in a conventional manner. The composition may be those suitable for oral administration, ocular topical administration, injection or perfusion as well as it may be an external agent.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary.

They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. Purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of injectable compositions of the present invention for parenteral administration include sterile aqueous or non-aqueous solutions, suspensions and emulsions.

Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization.

The injectable composition may also be provided as a sterilized powder composition to be dissolved in a sterilized solvent for injection before use.

The present compound may also be formulated as ophthalmic composition such as eye drops and eye ointments. The form may include all ophthalmic formulations for topical ocular administration used in the ophthalmic field.

The eye drops are prepared by dissolving active ingredients in a sterile aqueous solution such as saline and buffering solution. The eye drops may be provided as a powder composition to be dissolved before use, or by combining powder compositions to be dissolved before use. The eye ointments are prepared by mixing the active ingredient into an ointment base. The formulations are prepared according to the conventional methods.

Osmolarity modifiers include sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, boric acid, borax, sodium hydroxide, hydrochloric acid, mannitol, isosorbitol, propylene glycol, glucose and glycerine, but not limited thereto, as far as they are ordinarily used in the ophthalmic field.

Further, additives ordinarily used in the ophthalmic field may be added to the present composition as desired. Such additives include, for example, butter agent (e.g., boric acid, sodium monohydrogen phosphate and sodium dihydrogen phosphate), preservatives (e.g., benzalkonium chloride, benzethonium chloride and chlorobutanol), thickeners (e.g., saccharide such as lactose, mannitol and maltose; e.g., hyaluronic acid or its salt such as sodium hyaluronate and potassium hyaluronate; e.g., mucopolysaccharide such as chondroitin sulfate; e.g., sodium polyacrylate, carboxyvinyl polymer and crosslinked polyacrylate).

In preparing the present composition as an eye ointment, other than the above additives, the composition may contain ordinarily used eye ointment base. Such eye ointment base includes, but not limited to, oil base such as vaseline, liquid paraffin, polyethylene, selen 50, plastibase, macrogol or a combination thereof; emulsion base having oil phase and water phase emulsified with surfactant; and water soluble base such as hydroxypropylmethylcellulose, carboxypropylmethylcellulose and polyethylene glycol.

According to the present invention, the preferable embodiment includes that ophthalmic composition contains substantially no benzalkonium chloride. The phrase of "the ophthalmic composition contains substantially no benzalkonium chloride" used herein means that the composition contains no benzalkonium chloride, or the composition contains benzalkonium chloride as low as possible. In the present invention, the "ophthalmic composition containing substantially no benzalkonium chloride" may contain Benzalkonium chloride at a concentration of less than 0.01%, preferably 0.005% or less, more preferably 0.003% or less.

The present eye drops may be formulated as a sterile unit dose type formulation (one day type or single unit dose type) containing no preservatives such as benzalkonium chloride.

The ophthalmic composition further includes sustained release forms such as gel formulation, liposome formulation, lipid microemulsion formulation, microsphere formulation, nanosphere formulation and implant formulation in order to provide the active compound sustainedly to the back of the eye.

The concentration and administration number of the active ingredient of the eye drops used in the present invention may vary according to, for example, the compound to be used, the kind of subjects (such as animals or humans), age, weight, symptoms to be treated, effects of treatment to be desired, administration methods, administration volume and period of treatment. Accordingly, suitable concentration and administration number may be chosen as desired. Taking an example of isopropyl unoprostone, which is one form of the present invention, the formulation containing 0.01-1.0%, preferably 0.05-0.5%, more preferably at least 0.12%, 0.15% or 0.18% of isopropyl unoprostone may be ordinarily administered to an adult 1-10 times a day.

The term "treatment" used herein includes any means of control such as prevention, care, relief of the condition, attenuation of the condition and arrest of progression.

The pharmaceutical composition of the present invention may contain a single active ingredient or a combination of two or more active ingredients. In a combination of plural active ingredients, their respective contents may be suitably increased or decreased in consideration of their therapeutic effects and safety.

Further, the present formulations may suitably contain other pharmacologically active ingredients, as far as they are not contrary to the objects of the present invention.

The present invention will be described in detail with reference to the following example, which, however, is not intended to limit the scope of the present invention.

Example 1

Method

Human retinal pigment epithelium cells (ARPE-19 cells, purchased from American Type Culture Collection (ATCC)) were used in the study. ARPE-19 cells were grown on Corning Transwell 0.4 μm pore size filters (Corning Incorporated, NY, USA) in Dulbecco's modified Eagles medium containing 10% fetal calf serum. Trans-Epithelial Resistance (TER) of the cultured cells was determined using an EVOM volt-ohm meter. The TER of the cultured cells was determined by subtracting the resistance value measured with the filter alone from the value measured with the cultured cells.

The cells were grown until they reached a TER of approximately 50 Ohm/1.2 cm$^2$. They were then treated with 100 μM tert-butyl hydroperoxide (tBH) in 0.1% decane, 100 nM Compound A (isopropyl unoprostone, i.e. 13,14-dihydro-15-keto-20-ethyl-PGF$_{2\alpha}$ isopropyl ester) in DMSO (0.1% final DMSO), or a combination of tBH plus Compound A. TER was determined at 0, 6, 18, 24 and 48 hours after the treatment. Result is shown in FIG. 1.

ARPE-19 cells grown until they reached a TER of approximately 50 Ohm/1.2 cm$^2$ were treated with 100 μM tBH in 0.1% decane, 100 nM Compound A in DMSO (0.1% final DMSO), or a combination of tBH plus Compound A (initial treatment). At 20 hours after the initial treatment, 3,000 Dalton FITC-labeled dextran was added at a concentration of 0.1 mg/ml to the apical surface of the cell culture and the culture was further incubated. Fluorescence of the media bathing the basolateral surface was then measured at 44 hours. Wavelengths for FITC were 494 ex/518 em. The result is shown in FIG. 2.

Results tBH caused a rapid and large loss of TER. Compound A protected against the loss of TER caused by tBH (FIG. 1). Also Compound A protected against the loss of barrier function caused by tBH as measured by passage of 3,000 Dalton fluorescent dextran from the apical to basolateral media (FIG. 2). These results indicate that Compound A protects the damage of retinal pigment epithelium cells caused by reactive oxygen species.

The result indicates that compound A is useful for the treatment of macular degeneration especially AMD.

Example 2

Protection by Compound A from light induced cell death in pyridinium bis-retinoid (A2E) containing retinal pigment epithelium (RPE) cells Method Human retinal pigment epithelium cells (ARPE-19 cells) were used in the study. ARPE-19 cells were maintained in DMEM/F12 medium (supplemented with 10% FBS and 1% Penicillin-Streptomycin Mixed Sol.) in 25 cm$^2$ or 75 cm$^2$ culture flask. For the experiment, the cells were seeded on multi-well chamber slides. After confirming the cells adhered to slide, the media were changed to pyridinium bis-retinoid (A2E) containing culture medium and the cells were cultured for 5-14 days The media were changed to phosphate buffered saline (containing A2E), and then the cells were exposed to blue light (430 nm) delivered from a halogen source for 20 min. Compound A dissolved in dimethyl sulfoxide was added 1 hr before the light exposure (the final concentration was 10 and 50 nM). After the light exposure, the cells were cultured in the DMEM/F12 medium for 24 hours. The cells were then incubated in DMEM/F12 medium containing 10% WST-8 (without A2Z) for 4 hours. Absorbance at 450 nm was measured. An increase in the absorbance is indicative of cellular viability.

Results

Compound A prevented cell death induced by A2E/light exposure (Table 1).

TABLE 1

| Compound | Concentration | Condition | Cell Viability (%) |
|---|---|---|---|
| Vehicle (DMSO) | — | A2E + light exposure | 55 |
| Compound A | 50 nM | A2E + light exposure | 89 |
| Compound A | 10 nM | A2E + light exposure | 90 |

The result shown in Table 1 indicates that compound A is useful for the treatment of macular degeneration especially AMD.

Formulation Example 1

Ophthalmic solution was obtained by dissolving the ingredients in an amount shown below (w/v %) in purified water and filled in a sterilized low density polyethylene (LOPE) container under sterile condition (1 drop: approximately 35 μL).
0.15% 13,14-dihydro-15-keto-20-ethyl-PGF$_{2\alpha}$ isopropyl ester (isopropyl unoprostone)
1.0% polyoxyethylenesorbitan monooleate
1.0% mannitol
1.9% glycerin
0.05% edetate disodium
0.003% benzalkonium chloride Formulation Example 2

Sterile single unit dose ophthalmic solution was obtained by dissolving the ingredients in an amount shown below (w/v %) in purified water and filled in unit dose type container under sterile condition.
0.18% 13,14-dihydro-15-keto-20-ethyl-PGF$_{2\alpha}$ isopropyl ester (isopropyl unoprostone)
0.70% polyoxyethylenesorbitan monooleate
0.30% polyoxyl 10 oleyl ether
4.7% mannitol
0.01% edetate disodium Formulation Example 3

Sterile single unit dose ophthalmic solution was obtained by dissolving the ingredients in an amount shown below (w/v %) in purified water and dose unit type container under sterile condition.
0.24% 13,14-dihydro-15-keto-20-ethyl-PGF$_{2\alpha}$ isopropyl ester (isopropyl unoprostone)
0.95% polyoxyethylenesorbitan monooleate
0.42% polyoxyl 10 oleyl ether
4.7% mannitol
0.01% edetate disodium

What is claimed is:

1. A method for treating macular degeneration in a mammalian subject, which comprises administering to the mammalian subject in need of treatment for macular degeneration an effective amount of a single active ingredient for treating macular degeneration, wherein the single active ingredient is a 15-keto-prostaglandin compound which is a 13,14-dihydro-15-keto-20-ethyl-prostaglandin F2α isopropyl ester.

2. The method as described in claim 1, wherein said macular degeneration is age related macular degeneration.

3. The method as described in claim 2, wherein said age related macular degeneration is dry age related macular degeneration.

4. The method as described in claim 1, wherein the 15-keto-prostaglandin compound is formulated as a composition for topical administration.

5. The method as described in claim 4, wherein said composition is an ophthalmic composition for ocular topical administration.

6. The method as described in claim 5, wherein said ophthalmic composition is formulated as eye drop.

7. The method as described in claim 6, wherein said eye drop is formulated as a sterile unit dose type eye drop containing no preservatives.

8. The method as described in claim 5, wherein said ophthalmic composition comprises substantially no benzalkonium chloride.

* * * * *